(12) United States Patent
Laqua et al.

(10) Patent No.: US 6,410,778 B2
(45) Date of Patent: *Jun. 25, 2002

(54) METHOD OF PRODUCING ORGANIC DIURETHANES AND/OR POLYURETHANES AND THEIR USE IN THE PRODUCTION OF DI AND/OR POLYISOCYANATES

(75) Inventors: Gerhard Laqua, Limburgerhof; Ulrich Schoner, Schwarzheide; Andreas Otterbach, Frankenthal, all of (DE); Hans Volkmar Schwarz, Waterloo (BE)

(73) Assignee: BASF Aktiengesellschaft (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,361

(22) PCT Filed: Oct. 30, 1996

(86) PCT No.: PCT/EP96/04710

§ 371 (c)(1),
(2), (4) Date: May 7, 1998

(87) PCT Pub. No.: WO97/17323

PCT Pub. Date: May 15, 1997

(30) Foreign Application Priority Data

Nov. 7, 1995 (DE) .......................... 195 41 384

(51) Int. Cl.⁷ ............................................ C07C 269/00
(52) U.S. Cl. ....................... 560/115; 560/157; 560/158; 560/315
(58) Field of Search ................................ 560/115, 315, 560/157, 158

(56) References Cited

U.S. PATENT DOCUMENTS

| | | | | |
|---|---|---|---|---|
| 2,409,712 A | * | 10/1946 | Schweitzer | 560/345 |
| 2,806,051 A | * | 9/1957 | Brockway | 560/24 |
| 3,763,217 A | * | 10/1973 | Brill | 560/24 |
| 4,480,110 A | * | 10/1984 | Heitkamper et al. | 549/467 |
| 4,713,476 A | * | 12/1987 | Merger et al. | 560/115 |
| 4,851,565 A | * | 7/1989 | Merger et al. | 560/115 |

FOREIGN PATENT DOCUMENTS

| | | | |
|---|---|---|---|
| CA | 1144562 | * | 12/1983 |
| CA | 1166649 | * | 1/1984 |

\* cited by examiner

*Primary Examiner*—Paul J. Kilkos
*Assistant Examiner*—Taylor V. Oh
(74) *Attorney, Agent, or Firm*—Fernando Borrego

(57) ABSTRACT

Organic diurethanes and/or polyurethanes are prepared by reacting organic diamines and/or polyamines (a) with urea and/or alkyl cabamates (b) and alcohols (c) in the presence of soluble zirconium compounds, preferably zirconium alkoxides, zirconium acetate or zirconium acetylacetonate, as catalyst (d). They can be used for preparing diisocyanates and/or polyisocyanates by thermal dissociation.

7 Claims, No Drawings

METHOD OF PRODUCING ORGANIC DIURETHANES AND/OR POLYURETHANES AND THEIR USE IN THE PRODUCTION OF DI AND/OR POLYISOCYANATES

The present invention relates to a process for preparing organic diurethanes and/or polyurethanes, preferably aliphatic or cycloaliphatic diurethanes, by reacting the corresponding organic diamines and/or polyamines (a) with urea and/or alkyl carbamates (b) and alcohols (c) in the presence of soluble zirconium compounds such as zirconium alkoxides, zirconium acetate or zirconium acetylacetonate, as catalyst (d).

The present invention also relates to the use of diurethanes and/or polyurethanes prepared by the process of the present invention for preparing organic diisocyanates and/or polyisocyanates by thermal dissociation.

Organic polyisocyanates, such as aromatic, aliphatic or cycloaliphatic polyisocyanates, are valuable starting materials for producing polyisocyanate polyaddition products, for example polyurethane (PU) foams, surface coatings, dispersions, adhesives, polyisocyanurate (PIR) foams, thermoplastic PU elastomers (TPU) and compact or cellular PU- or PU-polyurea elastomers.

The industrial processes for preparing organic polyisocyanates are based on reaction of the corresponding organic polyamines with phosgene to give polycarbamic chlorides and thermal dissociation of the latter to give the polyisocyanates and hydrogen chloride and the thermal dissociation of monomeric diurethanes and/or polyurethanes into diisocyanates and/or polyisocyanates and alcohol.

Problems in the process using phosgene are, in particular, the high conversion of chlorine via phosgene and carbamic chloride into hydrogen chloride, the toxicity of the phosgene and the corrosiveness of the reaction mixture, the lability of the solvents generally used and the formation of halogen-containing residues.

There have therefore been many attempts to prepare organic isocyanates, preferably aromatic and (cyclo) aliphatic diisocyanates and/or higher-functional polyisocyanates, by a phosgene-free process.

According to EP-A-28 338 (U.S. Pat. No. 4,290,970) aromatic diisocyanates and/or polyisocyanates are prepared by a two-stage process in which, in the first reaction stage, primary aromatic diamines and/or polyamines are reacted with alkyl carbamates in the absence or presence of catalysts and the absence or presence of urea and alcohol to give aryl diurethanes and/or polyurethanes and the ammonia thus formed is, if desired, separated off, and the aryl diurethanes and/or polyurethanes obtained are converted in the second reaction stage into aromatic diisocyanates and/or polyisocyanates by thermal dissociation Continuous, multistage processes for the phosgene-free preparation of organic polyisocyanates are likewise known.

EP-A-0 355 443 (U.S. Pat. No. 5,087,739) relates to a circulation process for preparing (cyclo)aliphatic diisocyanates by conversion of the corresponding diamines into diurethanes and thermal dissociation of the latter, which reduces decreases in yield by the reaction mixture from the urethane dissociation stage being recirculated to the urethane formation stage after reaction with alcohol. By-products which cannot be recirculated are removed by distillative fractionation of the reaction mixture from the urethane formation stage; in this fractionation the unusable residue is obtained as bottom product and all lower-boiling components, including the diurethane, are taken off at the top.

EP-A-0 568 782 (U.S. Pat. No. 5,360,931) describes a multistage process for the continuous phosgene-free preparation of (cyclo)aliphatic diisocyanates, comprising the conversion of (cyclo)aliphatic diamines in a distillation reactor into the corresponding (cyclo)alkylenebisureas, their reaction with alcohol in a pressure distillation reactor to give the (cyclo)alkylene biscarbamates and the thermal dissociation of the latter in a combined dissociaton and rectification column to give the (cyclo)alkylene diisocyanates and alcohol in a liquid phase without use of solvents.

According to EP-A-0 566 925 (U.S. Pat. No. 5,386,053), a multistage process for preparing organic polyisocyanates comprises converting the organic polyamines into monomeric polyurethanes using carbonic acid derivatives and alcohols and thermally dissociating the monomeric polyurethanes. In certain reaction stages of this process, the polyisocyanates prepared and unusable residues are separated off and the reusable by-products are recirculated to earlier stages.

The economics of the continuous phosgene-free processes for preparing organic polyisocyanates is decisively influenced by the purity of the organic monomeric diurethanes and/or higher polyurethanes used for the thermal dissociation and the undesired secondary reactions, partly resulting from impurities and by-products, and the tendency of the reaction mixture to form deposits, of resinous material and blockages in reactors and work-up apparatus.

Organic monomeric diurethanes and/or higher polyurethanes can be prepared by reacting organic polyamines with carbonic acid derivatives, preferably urea and/or alkyl carbamates, and alcohols in the absence or presence of catalysts.

According to EP-B-0 018 586 (U.S. Pat. No. 4,713,476 and U.S. Pat. No. 4,851,565) aliphatic and/or cycloaliphatic diurethanes and/or polyurethanes can be prepared by reacting the corresponding polyamines with urea and alcohols in the presence of catalysts. In a similar manner, according to EP-B-0 019 109 (U.S. Pat. No. 4,611,079), aromatic diurethanes and/or polyurethanes can be obtained using aromatic polyamines. Suitable catalysts mentioned are inorganic or organic compounds containing one or more cations of metals of groups IA, IB, IIA, IIB, IIIA, IIIB, IVA, IVB, VA, VB, VIB, VIIB and VIIIB of the Periodic Table, eg. halides, sulfates, phosphates, nitrates, borates, alkoxides, phenoxides, sulfonates, oxides, hydrated oxides, hydroxides, carboxylates, chelates, carbonates and thio- or dithiocarbamates. Aryl mono-, di- and/or polyurethanes can, according to EP-B-0 018 538 (U.S. Pat. No. 4,278,805 and U.S. Pat. No. 4,375,000), be prepared by reacting corresponding primary aromatic monoamines or polyamines with alkyl carbamates in the presence of the abovementioned catalysts.

N,O-disubstituted urethanes can, according to EP-A-0 028 331 (U.S. Pat. No. 4,480,110), be prepared by reacting mixtures of substituted ureas and N-unsubstituted urethanes and/or urea and/or polyurets with alcohols in the presence of esterification catalysts for carboxylic acids. According to EP-B-0 027 940 (CA-A-1 144 562), urethanes can be prepared by reacting urea or polyurets with primary amines and alcohols in the presence of compounds which exercise a catalytic influence on the esterification reaction of carboxylic acids with alcohols and which also have an accelerating action on the urethane reaction. Suitable catalysts mentioned are: inorganic and organic bases which are inert under the reaction conditions, Lewis acids and salts or complexes, in particular chelates of transition metals. Among numerous catalysts which can be used, mention is also made, by way of example, of coordination compounds of iron, nickel, cobalt, zinc, manganese, molybdenum, titanium, zirconium, thorium, hafnium and vanadium with β-diketones, eg. acetylacetone and β-ketoesters. The best catalytic activity was shown by zinc octoate with a conversion of 97 mol %, while iron acetylacetonate with 90 mol % gave a comparatively low catalytic effect, particularly for industrial-scale processes.

To ensure sufficient quality of the organic diurethanes and/or higher polyurethanes for a thermal dissociation to give organic polyisocyanates, it is desirable to have preparative processes for polyurethanes which ensure both a high space-time yield and a high selectivity, eg. of ≧98 mol % of polyurethane, based on the organic polyamine used.

Partially reacted intermediates containing urea groups cause considerable interference in the urethane dissociation to give the polyisocyanate and can be separated from the polyurethane formed only with difficulty.

It is an object of the present invention to prepare diurethanes and/or higher polyurethanes in very high space-time yields with high selectivities in order to inexpensively convert these into polyisocyanates by thermal dissociation under optimum reaction conditions.

We have found that this object is achieved by a special urethane catalysis.

The present invention accordingly provides a process for preparing organic diurethanes and/or higher polyurethanes, preferably aliphatic or cycloaliphatic diurethanes and/or higher polyurethanes, in particular aliphatic or cycloaliphatic diurethanes, by reacting a) organic diamines and/or polyamines, preferably aliphatic or cycloaliphatic diamines, with
b) urea and/or alkyl carbamates and
c) alcohols in the presence of a
d) catalyst, wherein the catalyst (d) used comprises zirconium compounds soluble in the reaction mixture.

Since the reactor volumes required for the preparation of a certain amount of diurethanes and/or polyurethanes is directly dependent on the space-time yield of the reaction, the catalysis can be optimized by use of the soluble zirconium compounds of the present invention. This results in the following ecomonomic advantages: the costs of the production plant can be minimized, the polyurethane yield can be increased in existing production plants and/or defined amounts of polyurethane can be produced with maximum selectivity in existing production plants. Under identical reaction conditions, the process of the present invention makes possible an increase in the space-time yield by a factor of 3 in comparison with the uncatalyzed reaction and by a factor of 2 when using the zirconium acetate of the present invention in comparison with aluminum acetylacetonate as described in EP-B-0 027 940. The process of the present invention enables monomeric diurethanes and/or polyurethanes, in particular aliphatic and cycloaliphatic diurethanes, to be prepared advantageously in high space-time yields and with maximum selectivity, thereby minimizing the production costs.

According to the present invention, catalysts used are zirconium compounds which are soluble in the reaction mixture, particularly under the reaction conditions employed. Examples of suitable soluble zirconium compounds are zirconium alkoxides of linear or branched alcohols having from 1 to 10 carbon atoms, preferably from 1 to 4 carbon atoms, for example zirconium methanolate, ethanolate, n- and iso-propanolate, n-butanolate, sec-butanolate, tert-butanolate, isomeric zirconium pentanolates, such as tetrapentanolate, 2-methyl-2-butanolate, hexanolate, 2-ethylhexanolate, tetra-2-ethylhexanolate, octanolate, decanolate and preferably zirconiumn n-butanolate, amine-substituted zirconium compounds, such as tetradiethylaminozirconium, acetylacetonates, such as zirconium acetylacetonate, zirconium tetra-2-ethylhexanoate, zirconium(IV) trifluoroacetylacetonate, tetrakis(2,2,6,6-tetramethyl-3,5-heptanedionato)zirconium, zirconium hexafluoroacetylacetonate, carboxylates of zirconium, such as zirconium acetate, zirconium oxalate, zirconyl propionate, zirconium butyrate and isomers thereof, zirconium tetraacrylate, zirconium methacrylate, zirconium dimethacrylate dipropanolate, zirconium(IV) dimethacrylate, zirconium methacryloxyethylacetoacetate tri-n-propanolate and higher carboxylates, such as zirconium citrates, zirconium lactate, zirconium neodecanoate, cyclopentadienyl complexes of zirconium, such as zirconocene diethoxide, zirconocene dichloride, zirconocene chloride hydride, cyclopentadienylzirconium trichloride, bis(pentamethylcyclopentadienyl)zirconium dichloride, pentamethylcyclopentadienylzirconium trichloride, zirconcene bis(trifluoromethanesulfonate), zirconium salts of inorganic acids such as zirconium carbonate, zirconium hydroxide, zirconium nitrate, zirconium sulfate, zirconium sulfide, zirconium phosphate, zirconium pyrophosphate, zirconyl ammonium carbonate, zirconium halides such as zirconium (IV) fluoride, zirconium(IV) chloride, zirconium tetrabromide, zirconium tetraiodide, zirconyl chloride, zirconyl perchlorate, sodium hexafluorozirconate, zirconates, such as aluminum zirconate, ammonium hexafluorozirconate, bismuth zirconate, lead zirconate, cadmium zirconate, cesium zirconate, calcium zirconate, cerium zirconate, cobalt zirconate, potassium hexafluorozirconate, potassium pentafluorozirconate, lithium zirconate, magnesium zirconate, manganese zirconate, sodium zirconate, rubidium zirconate, strontium zirconate, zinc zirconate and other inorganic zirconium compounds such as zirconium aluminide, zirconium boride, zirconium hydride, zirconium carbide, zirconium molybdate, zirconium nitride, zirconium selenide, zirconium telluride and zirconium tungstate.

Compounds which have been found to be very useful and are therefore preferably used are: zirconium acetate, zirconium acetylacetonate and, in particular, zirconium-n-butanolate.

The catalysts can be used in any amounts. For economic reasons, very small amounts of catalyst are advantageously used. Depending on their catalytic activity, which can easily be measured experimentally, the zirconium compounds are advantageously used in an amount of from 0.00001 to 1 mol percent, preferably from 0.0001 to 0.1 mol percent and in particular from 0.001 to 0.05 mol percent.

The organic monomeric diurethanes and/or polyurethanes can be prepared in the presence of the catalysts of the present invention according to known methods by reacting polyamines with carbonic acid derivatives, in particular urea, and alcohols with removal of the ammonia formed.

Viewed purely formally, the process of the present invention can be represented by the following equation:

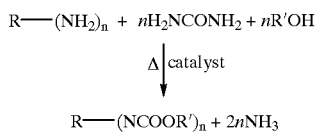

a) Examples of suitable amines of the formula R—(NH$_2$)$_n$, where R is a polyvalent, unsubstituted or substituted organic, preferably aromatic and in particular aliphatic or cycloaliphatic, radical and n is an integer which corresponds to the valence of R and is at least 2, preferably from 2 to 5 and in particular 2, are: aromatic polyamines which may be unsubstituted or substituted on the arylene radical by, for example, $C_1$-$C_4$-alkyl, $C_1$-$C_4$-alkoxy or halogen, for example 2,4- and 2,6-tolylenediamines or their industrial mixtures, 2,2'-, 2,4'- and preferably 4,4'-diaminodiphenylmethane or mixtures of at least 2 of the specified isomers, 3,3'-dimethyl-4,4'-diaminobiphenyl, 1,2-bis(4-aminophenyl)ethane, 1,3- and 1,4-phenylenediamine, 1,4- and 1,5-diaminonaphthalene, 3,3',5,5'-tetraethyl-, 3,3', 5,5'-tetraisopropyl-4,4'-diaminodiphenylmethane, 1,3,5-triaminobenzene, 2,4,6-triaminotoluene and polyphenylpolymethylenepolyamines and also mixtures of Diaminodiphenylmethanes and polyphenylpolymethylenepolyamines, which can be obtained according to known methods by condensation of aniline and formaldehyde in the presence of, preferably, mineral acids as catalyst or in the absence of catalysts, aliphatic polyamines having from 2 to 19 carbon atoms, preferably from 3 to 13 carbon atoms and in particular from 4 to 6 carbon atoms; these can have a straight-chain or branched structure and contain as bridges heteroatoms, eg. oxygen or sulfur, or divalent heterocyclic radicals or arylene, preferably phenylene, radicals in bonded form, for example ethylenediamine, 1,3- and 1,2-Propylenediamine, 2,2-dimethylpropylene-1,3-diamine, 1,4-butylenediamine, 2-ethylbutylene-1,4-diamine, 2-ethyl-2-butylbutylene-1,4-diamine, 1,5-pentamethylenediamine, 2-methylpentamethylene-1,5-diamine, 2-ethyl-2-butylpentamethylene-1,5-diamine, 1,6-hexamethylenediamine, 2,2,4-trimethylhexamethylene-1,6-diamine, 1,8-octamethylenediamine, 1,10-decylenediamine, 1,12-dodecylenediamine, hexahydroxylylene-1,4-diamine and 1,4-xylylenediamine, and cycloaliphatic polyamines having from 5 to 12 carbon atoms, preferably from 6 to 12 carbon atoms, for example 1,2-, 1,3- and 1,4-cyclohexanediamine, hexahydrotolylene-2,4- and -2,6-diamine and also the corresponding isomer mixtures, 4,4'-, 2,4'- and 2,2'-diaminodicyclohexylmethane and also the corresponding isomer mixtures and 3-aminomethyl-3,5,5-trimethylcyclohexylamine. As polyamines, preferably diamines, preference is given to using 2,4- and 2,6-tolylenediamine, 4,4'-, 2,4'- and 2,2'-diaminodiphenylmethane and their isomer mixtures and also, in particular, 1,6-hexamethylenediamine and 3-aminomethyl-3,5,5-trimethylcyclohexylamine.

b) As carbonic acid derivative, preference is given to using urea (b). Since urea forms an alkyl carbamate with alcohol under the reaction conditions employed in the urethane formation, it is also possible to use an alkyl carbamate as formative component (b) in place of urea or together with urea. An alkyl carbamate can be prepared in a preliminary stage, for example from urea and alcohol which is advantageously used in excess, and this ester, for example in the form of an alcoholic solution, can be reacted with the polyamines in the presence of the soluble zirconium compounds as catalyst. In a similar manner dialkyl carbonates formed as by-products in the urethane formation or prepared separately can also be used, so that mixtures of urea, alkyl carbamates and/or dialkyl carbonate can be employed in place of urea.

Suitable alkyl carbamates have the formula $H_2N$—COOR, where R is an unsubstituted or substituted aliphatic, cycloaliphatic or aromatic-aliphatic radical. Examples of suitable compounds are alkyl carbamates based on primary aliphatic monoalcohols having from 1 to 20 carbon atoms, preferably from 1 to 10 carbon atoms, for example methyl carbamate, ethyl carbamate, propyl carbamate, n-butyl carbamate, isobutyl carbamate, 2- and 3-methylbutyl carbamate, neopentyl carbamate, pentyl carbamate, 2-methylpentyl carbamate, n-hexyl carbamate, 2-ethylhexyl carbamate, heptyl carbamate, n-octyl carbamate, n-nonyl carbamate, n-decyl carbamate and n-dodecylcarbamate, 2-phenylpropyl carbamate and benzyl carbamate and based on secondary aliphatic and cycloaliphatic monoalcohols having from 3 to 15 carbon atoms, preferably from 3 to 6 carbon atoms, for example isopropyl carbamate, sec-butyl carbamate, sec-iso-amyl carbamate, cyclopentyl carbamate, cyclohexyl carbamate, tert-butylcyclohexyl carbamate and bicyclo[2.2.1]heptyl carbamate. Preference is given to using methyl carbamate, ethyl carbamate, propyl carbamate, butyl carbamate, isobutyl carbamate, 2- and 3-methylbutyl carbamate, pentyl carbamate, hexyl carbamate, 2-ethylhexyl carbamate, heptyl carbamate, octyl carbamate and cyclohexyl carbamate.

If the urethane formation is carried out using urea in the presence of dialkyl carbonates or preferably alkyl carbamates, the dialkyl carbonates can be used, for example, in an amount of from 0.1 to 30 mol %, preferably from 1 to 10 mol %, or the alkyl carbamates can be used, for example, in an amount of from 1 to 20 mol %, preferably from 5 to 15 mol %, based on the polyamine, preferably diamine. However, particular preference is given to using mixtures of dialkyl carbonates and alkyl carbamates in the specified ratios. The dialkyl carbonates and/or carbamic esters used are preferably ones whose alkyl radicals correspond to the alkyl radical of the alcohol used.

The preparation of the monomeric organic polyurethanes, preferably diurethanes, can also be carried out in the presence of other carbonic acid derivatives, eg. polyurets, substituted ureas, unsubstituted and substituted polyureas, oligourea-polyurethanes, high-boiling oligomers and other by-products formed in the thermal dissociation of the diurethanes and/or polyurethanes to give diisocyanates and/or polyisocyanates. These carbonic acid derivatives can, for example, be formed in the thermal dissociation of the polyurethanes, isolated, if desired subjected to intermediate storage or can be prepared in separate processes and, if desired together with the urea (b) and/or alcohol (c), be introduced into the polyurethane preparation. In continuous processes for preparing organic polyisocyanates by thermal dissociation of polyurethanes, such carbonic acid derivates from the dissociation reactor can be recirculated to the urethane formation.

c) Alcohols (c) which can be used for the process of the present invention are any unsubstituted or substituted primary or secondary aliphatic alcohols or aromatic-aliphatic alcohols and also mixtures thereof. However, since the diurethanes and/or polyurethanes are used in particular for preparing polyisocyanates, it is preferably to select those whose boiling points are sufficiently far from the boiling point of the polyisocyanate, preferably diisocyanate, obtained by the thermal dissociation, so that a virtually quantitative separation of the dissociation products polyisocyanate, preferably diisocyanate, and alcohol is possible.

For these reasons, preference is given to using primary aliphatic monoalcohols having from 1 to 20 carbon atoms, preferably from 1 to 10 carbon atoms, for example methanol, ethanol, propanol, n-butanol, iso-butanol, 2- and 3-methylbutanol, neopentyl alcohol, pentanol, 2-methylpentanol, n-hexanol, 2-ethylhexanol, n-heptanol, n-octanol, n-nonanol, n-decanol, n-dodecanol, 2-phenylpropanol and benzyl alcohol, secondary aliphatic and cycloaliphatic monoalcohols having from 3 to 15 carbon atoms, preferably from 3 to 6 carbon atoms, for example isopropanol, sec-butanol, sec-isoamyl alcohol, cyclopentanol, cyclohexanol, 2,3- or 4-methylcyclohexanol and 4-tert-butylcyclohexanol, or mixtures of the alcohols specified, but in particular n-butanol and/or iso-butanol.

To prepare the diurethanes and/or polyurethanes by the process of the present invention, the primary organic diamines and/or polyamines (a), preferably aliphatic or cycloaliphatic diamines, can be reacted with urea (b) and alcohol (c) in such amounts that the ratio of $NH_2$ groups of the amines to urea (b) and any alkyl carbamate and/or dialkyl carbonate to hydroxyl groups of the alcohols (c) is 1:0.7-5:1-50, preferably 1:0.9-2:1-10 and in particular 1:1.0 to 1.3:1.5-5. If the reaction is carried out in the presence of dialkyl carbonates and/or preferably alkyl carbamates, 1 mol of alkyl carbamate or dialkyl carbonate can be used in place of 1 mol of urea. The reaction in the presence of the soluble zirconium compounds as catalyst is usually carried out in the range from 160° to 300° C., preferably from 180° to 250° C. and in particular from 185° to 240° C. and under a pressure which is, depending on the alcohol used, from 0.1 to 60 bar, preferably from 1 to 40 bar. These reaction conditions give reaction times of, for example, from 0.5 to 48 hours, preferably from 1 to 3 hours.

The reaction is advantageously carried out in the presence of excess alcohol as solvent and reaction medium. It has here found to be advantageous to immediately remove the ammonia formed from the reaction mixture, for example by distillation. An apparatus used for this purpose, eg. a distillation column, can be operated at from 60 to 150° C., preferably from 65 to 120° C., so that deposition of ammonium carbamate, which is formed in small amounts from ammonia and carbon dioxide from decomposition of urea, can be avoided.

The diurethane and/or polyurethane preparation can be carried out batchwise or continuously. In the case of the continuous procedure, it has been found to be advantageous to separate the alcohol, the dialkyl carbonates, in so far as these have been formed or are present in the reaction mixture, or alkyl carbamates or mixtures of at least two of these components from the reaction mixture after the urethane formation is complete and preferably recirculate them to the beginning of the reaction. To separate off the components, the reaction mixture is advantageously depressurized from the pressure level at the beginning of the reaction to a pressure in the range from 1 to 500 mbar, preferably from 10 to 100 mbar. This gives gaseous vapors containing most of the alcohol and from 0 to 30% by weight, preferably from 1 to 10% by weight, of dialkyl carbonate and/or from 1 to 50% by weight, preferably from 1 to 20% by weight, of alkyl carbamate, and a liquid product consisting essentially of the monomeric polyurethane, preferably diurethane, and possibly oligourea-polyurethanes and high-boiling oligomers.

The vapors obtained can be fractionated in subsequent purification steps, advantageously by distillation, preferably by rectification, and the useful products thus isolated, viz. alcohol and alkyl carbamate, individually or as a mixture, can preferably be recirculated to the beginning of the reaction to form the monomeric polyurethanes.

The liquid product can be separated by distillation, eg. using a conventional distillation unit, preferably a thin-film evaporator, at, for example, from 170° to 240° C., preferably from 180° to 230° C. and under a pressure of from 0.01 to 5 mbar, preferably from 0.1 to 2 mbar, into a useful product containing the polyurethanes, preferably diurethanes, and the lower-boiling by-products, and an unusable residue which is discarded.

The useful product can be converted directly into diisocyanates and/or polyisocyanates by thermal dissociation or the lower-boiling by-products can be separated off, eg. by distillation, and the diurethanes and/or polyurethanes obtained can be additionally purified by distillation or recrystallization, advantageously from other solvents.

The organic polyurethanes, preferably diurethanes, prepared by the process of the present invention are preferably used for preparing organic polyisocyanates which in turn are used for preparing polyisocyanate polyaddition products.

EXAMPLES

Comparative Example I

In a 1.5 l stirring autoclave fitted with a pressure maintenance device and a reflux condenser operated using water heated to 90° C., 104.4 g (0.9 mol) of hexamethylenediamine (HDA), 135 g (2.25 mol) of urea and 532.8 g (7.2 mol) of n-butanol were reacted at 210° C. under reflux and under a pressure of 9 bar.

The ammonia formed was continuously removed from the reaction mixture.

The course of the reaction was monitored by taking samples from the reaction mixture every hour and analyzing them by liquid chromatography.

After a reaction time of 6 hours, the reaction system was still not in a steady state with regard to all by-products formed. The hexamethylenediurethane (HDU) content of the reaction product (660 g) was 40% by weight. This gave a space-time yield of less than 53 [g/l·h].

Comparative Example II

The procedure of Comparative Example I was repeated, but the reaction was carried out in the presence of 14.6 mg of aluminum acetylacetonate (0.005 mol %, based on HDA).

The reaction system had reached a steady state after 4 hours, with the HDU content of the reaction product (661 g) being 40% by weight. This gave space-time yield of 80 [g/l·h].

Comparative Example III

The procedure of Comparative Example I was repeated, but the reaction was carried out in the presence of 16 mg of iron acetylacetonate (0.005 mol %, based on HDA).

The reaction system had reached a steady state after 4 hours, with the HDU content of the reaction product (660 g) being 41% by weight. This gave a space-time yield of 82 [g/l·h].

Example 1

The procedure of Comparative Example I was repeated, but the reaction was carried out in the presence of 22 mg of zirconium acetylacetonate (0.005 mol %, based on HDA).

The reaction system had reached a steady state after 2 hours, with the HDU content of the reaction product (663 g) being 41% by weight. This gave a space-time yield of 164 [g/l·h].

Example 2

The procedure of Comparative Example I was repeated, but the reaction was carried out in the presence of 10 mg of zirconium acetate $(Zr(C_2H_3O_2)_{1.4}(OH)_{2.6})$ (0.005 mol %, based on HDA).

The reaction system had reached a steady state after 2 hours, with the HDU content of the reaction product (662 g) being 42% by weight. This gave a space-time yield of 168 [g/l·h].

Example 3

The procedure of Comparative Example I was repeated, but the reaction was carried out in the presence of 21.6 mg of an 80% strength by weight zirconium butanolate solution in n-butanol (0.005 mol %, based on HDA).

The reaction system had reached a steady state after 2 hours, with the HDU content of the reaction product (662 g) being 43% by weight. This gave a space-time yield of 172 [g/l·h].

Comparative Example IV

In a 1.5 l stirring autoclave fitted with a pressure maintenance device and a reflux condenser operated using water heated to 90° C., 170 g (1 mol) of isophoronediamine (IPDA), 150 g (2.50 mol) of urea and 592 g (8.0 mol) of n-butanol were reacted at 210° C. under reflux and under a pressure of 8 bar. The ammonia formed was continuously removed from the reaction mixture.

The course of the reaction was monitored by taking samples from the reaction mixture every hour and analyzing them by liquid chromatography.

After a reaction time of 6 hours, the reaction system was still not in a steady state with regard to all by-products formed. The space-time yield was less than 60 [g/l·h].

Example 4

The procedure of Comparative Example IV was repeated, but the reaction was carried out in the presence of 24.4 mg of zirconium acetylacetonate (0.005 mol %, based on IPDA).

The reaction system had reached a steady state after 2 hours, giving a space-time yield of 170 [g/l·h] of isophoronediurethane (IPDU).

Comparative Example V

In a 1.5 l stirring autoclave fitted with a pressure maintenance device and a reflux condenser operated using water heated to 90° C., 104.4 g (0.9 mol) of HDA, 263 g (2.25 mol) of n-butyl carbamate and 366 g (4.95 mol) of n-butanol in the presence of 14.6 mg of aluminum acetyl acetonate (0.005 mol %, based on HDA) were reacted at 210° C. under reflux and under a pressure of 9 bar. The ammonia formed was continuously removed from the reaction mixture.

The course of the reaction was monitored by taking samples from the reaction mixture every hour and analyzing them by liquid chromatography.

After a reaction time of 6 hours, the reaction system was still not in a steady state with regard to all by-products formed. The HDU content of the reaction product (665 g) was 40.4% by weight. This gave a space-time yield of less than 54 [g/l·h].

Example 5

The procedure of Comparative Example V was repeated, but the reaction was carried out in the presence of 21.9 mg of zirconium acetylacetonate (0.005 mol %, based on HDA).

The reaction system had reached a steady state after 4 hours, with the HDU content of the reaction product (663 g) being 42.6% by weight. This gave a space-time yield of 83 [g/l·h].

Comparative Example VI

In a cascade of 4 stirred reactors, 600 g/h of HDA, 700 g/h of urea and 2200 g/h of n-butanol were reacted continuously under the following conditions:

| | |
|---|---|
| 1st stirred reactor: | volume: 25 l |
| | pressure: 11 bar |
| | temperature: 218° C. |
| feed: | 600 g/h of HDA |
| | 700 g/h of urea |
| | 2200 g/h of n-butanol |
| condensate: | 14 l/h n-butanol |
| 2nd stirred reactor: | volume: 12.5 l |
| | pressure: 11 bar |
| | temperature: 222° C. |
| 3rd stirred reactor: | volume: 12.5 l |
| | pressure: 11 bar |
| | temperature: 227° C. |
| 4th stirred reactor: | volume: 12.5 l |
| | pressure: 11 bar |
| | temperature: 230° C. |

The HDU content of the reaction product from the cascade (3100 g/h) was 51.6% by weight, giving a space-time yield of 26 [g/l·h]. The HDU yield, based on HDA used, was 97.9%.

Comparative Example VII

In a cascade of 4 stirred reactors, 1000 g/h of HDA, 1200 g/h of urea and 3700 g/h of n-butanol were reacted continuously under the following conditions:

| | |
|---|---|
| 1st stirred reactor: | volume: 25 l |
| | pressure: 11 bar |
| | temperature: 218° C. |
| feed: | 1000 g/h of HDA |
| | 1200 g/h of urea |
| | 3700 g/h of n-butanol |
| condensate: | 20 l/h of n-butanol |
| catalyst: | 418 mg of aluminum acetylacetonate |
| | (0.015 mol %, based on HDA) |
| 2nd stirred reactor: | volume: 12.5 l |
| | pressure: 11 bar |
| | temperature: 222° C. |

-continued

```
3rd stirred reactor:  volume: 12.5 l
                      pressure: 11 bar
                      temperature: 227° C.
4th stirred reactor:  volume: 12.5 l
                      pressure: 11 bar
                      temperature: 230° C.
```

The HDU content of the reaction product from the cascade (5200 g/h) was 49.4% by weight, giving a space-time yield of 41 [g/l·h]. The HDU yield, based on HDA used, was 94.3%.

Example 6

In a cascade of 4 stirred reactors,
1300 g/h of HDA,
1550 g/h of urea and
4800 g/h of n-butanol
were reacted continuously under the following conditions:

```
1st stirred reactor:  volume: 25 l
                      pressure: 11 bar
                      temperature: 218° C.
               feed:  1300 g/h of HDA
                      1550 g/h of urea
                      4800 g/h of n-butanol
         condensate:  26 l/h of n-butanol
           catalyst:  127 mg of zirconium acetate (0.005 mol %,
                      based on HDA)
2nd stirred reactor:  volume: 12.5 l
                      pressure: 11 bar
                      temperature: 222° C.
3rd stirred reactor:  volume: 12.5 l
                      pressure: 11 bar
                      temperature: 227° C.
4th stirred reactor:  volume: 12.5 l
                      pressure: 11 bar
                      temperature: 230° C.
```

The HDU content of the reaction product from the cascade (6800 g/h) was 51.0% by weight, giving a space-time yield of 56 [g/l·h]. The HDU yield, based on HDA used, was 98.0%.

The Comparative Examples VI and VII and Example 6 show that in a given, continuously operated cascade of stirred reactors the high HDU yields required for the subsequent dissociations are achieved in the highest space-time yield using the soluble zirconium compounds of the present invention as catalyst. In comparison with the uncatalyzed reaction (Comparative Example VI), the zirconium acetate used as catalyst according to the present invention (Example 6) enables the same cascade of stirred reactors to be operated at more than double the loading while maintaining the prescribed HDU quality.

We claim:

1. A process for preparing aliphatic and/or cycloaliphatic organic diurethanes and/or polyurethanes by reacting a) aliphatic and/or cycloaliphatic organic di- and/or polyamines with b) urea, alkyl carbamates or mixtures of urea, alkyl carbamates and/or dialkyl carbonates; and c) alcohol in the presence of a d) catalyst, wherein the catalyst used comprises zirconium compounds as the catalyst in an amount of from 0.00001 to 1 mol %, based on the diamines and/or polyamines.

2. A process as claimed in claim 1, wherein the soluble zirconium compounds used are zirconium-n-butoxide, zirconium acetate or zirconium acetylacetonate.

3. A process as claimed in claim 1, wherein the organic diamines are selected from the group consisting of 1,6-hexanediamine and 3-aminomethyl-3,5,5-trimethylcyclohexylamine.

4. A process as claimed in claim 1, wherein the diamines and/or polyamines (a), urea (b) and alcohols (c) are reacted in such amounts that the ratio of $NH_2$ groups of the diamines and/or polyamines (a) to urea (b) to hydroxyl groups of the alcohols (c) is 1:0.7–5:1–50.

5. A process as claimed in claim 1, wherein the reaction is carried out at a temperature of from 160° C. to 300° C. and a pressure of from 0.1 to 60 bar.

6. A process as claimed in claim 1, wherein the reaction is carried out in the presence of polyurets, substituted ureas, substituted and unsubstituted polyureas, oligourea-polyurethanes, high-boiling oligomers and other by-products formed in the thermal dissociation of the diurethanes and/or polyurethanes to give diisocyanates and/or polyisocyanates.

7. A process as claimed in claim 1, wherein the zirconium compound catalyst is present in an amount of from 0.0001 to 0.1% by mole, based on the diamines and/or polyamines.

* * * * *